US006656114B1

(12) United States Patent
Poulsen et al.

(10) Patent No.: US 6,656,114 B1
(45) Date of Patent: Dec. 2, 2003

(54) METHOD AND A SYSTEM FOR ASSISTING A USER IN A MEDICAL SELF TREATMENT, SAID SELF TREATMENT COMPRISING A PLURALITY OF ACTIONS

(75) Inventors: Jens Ulrik Poulsen, Virum (DK); Lars Hofmann Christensen, Jyllinge (DK); Søren Aasmul, Holte (DK)

(73) Assignee: Novo Noadisk A/S, Bagsvaerd (DK)

( * ) Notice: Subject to any disclaimer, the term of this patent is extended or adjusted under 35 U.S.C. 154(b) by 0 days.

(21) Appl. No.: 09/462,128

(22) PCT Filed: Nov. 30, 1999

(86) PCT No.: PCT/DK99/00670

§ 371 (c)(1),
(2), (4) Date: Oct. 30, 2000

(87) PCT Pub. No.: WO00/32258

PCT Pub. Date: Jun. 8, 2000

Related U.S. Application Data

(60) Provisional application No. 60/111,721, filed on Dec. 9, 1998.

(30) Foreign Application Priority Data

Nov. 30, 1998 (DK) .......................... 1998 01578

(51) Int. Cl.⁷ ............................ A61B 5/00; G06F 17/60
(52) U.S. Cl. ...................... 600/300; 600/301; 600/316; 128/920; 705/3
(58) Field of Search .................... 702/19; 705/2–4; 600/300–301, 316, 347, 365; 604/65–66; 128/920–925, 904, 897; 340/573.1; 700/242

(56) References Cited

U.S. PATENT DOCUMENTS

| 3,786,510 | A | * | 1/1974 | Hodges | .................... 600/584 |
| 4,523,297 | A | * | 6/1985 | Ugon et al. | ................. 235/380 |
| 4,731,726 | A |   | 3/1988 | Allen, III | |
| 5,204,670 | A |   | 4/1993 | Stinton | |
| 5,216,597 | A |   | 6/1993 | Beckers | |
| 5,313,941 | A | * | 5/1994 | Braig et al. | .................. 600/316 |
| 5,371,687 | A | * | 12/1994 | Holmes, II et al. | ........... 710/72 |
| 5,536,249 | A | * | 7/1996 | Castellano et al. | ........... 604/65 |
| 5,549,117 | A | * | 8/1996 | Tacklind et al. | ............ 600/533 |
| 5,672,154 | A | * | 9/1997 | Sillen et al. | ................. 604/503 |
| 5,673,691 | A |   | 10/1997 | Abrams et al. | |
| 5,687,717 | A | * | 11/1997 | Halpern et al. | .............. 128/903 |
| 5,822,715 | A | * | 10/1998 | Worthington et al. | .......... 702/19 |
| 5,842,976 | A | * | 12/1998 | Williamson | .................. 600/300 |
| 5,956,501 | A |   | 9/1999 | Brown | |
| 6,155,975 | A | * | 12/2000 | Urich et al. | ................. 600/300 |
| 6,363,416 | B1 | * | 3/2002 | Naeimi et al. | .............. 709/209 |

FOREIGN PATENT DOCUMENTS

| WO | WO92/12490 | 7/1992 |
| WO | WO96/37246 | 11/1996 |
| WO | WO98/02086 | 1/1998 |

OTHER PUBLICATIONS

CA 1296068 C (Friesen EJ) Feb. 18, 1992 (abstract), World Patents Index (online), London, U.K., Derwent Publications, Ltd. (retrieved from: EPO WPI database DW9214, Accession No. 92–105121).

* cited by examiner

Primary Examiner—Max F. Hindenburg
Assistant Examiner—Michael Astorino
(74) Attorney, Agent, or Firm—Reza Green, Esq.; Richard W. Bosk, Esq.; Marc A. Began, Esq.

(57) ABSTRACT

A method of self treating a disease, such as diabetes, includes collecting in one or more databases data representing values of parameters that related to the self treatment. The data is processed to provide a plurality of alternate choices between two or more actions that may be taken and a corresponding value for each action is calculated. A computerized system may be employed to perform the above method and the system may include a computer readable medium for executing the method.

46 Claims, 9 Drawing Sheets

| | | Proposals | User input | Proposals | User input | Proposals | |
|---|---|---|---|---|---|---|---|
| 205  | ... | 10IU | 5IU | 5IU | | 0 | ... |
| 206  | ... | 0 | | 0 | | 0 | ... |
| 207  | ... | 2 tablets | | 1 tablet | | 0 | ... |
| 208  | ... | 60min | | 30min | 30min | 0 | ... |
| 209  | ... | 0 | | 0 | | 0 | ... |
| 210  | ... | 0 | | 0 | | 0 | ... |

|  | | Value | Value | Value | Value | Value |  |
|---|---|---|---|---|---|---|---|
| BGM | ... | 10.5 mmol/l | - | - | - | - | ... |
| [bed icon] | ... | 37.5° | - | - | - | - | ... |

▦ BGL
▨ Insulin
▧ Suggested insulin, blinking

METHOD AND A SYSTEM FOR ASSISTING A USER IN A MEDICAL SELF TREATMENT, SAID SELF TREATMENT COMPRISING A PLURALITY OF ACTIONS

CROSS-REFERENCE TO RELATED APPLICATIONS

This application claims the benefit of priority under 35 USC §119 of Danish Application 1998 01578, filed Nov. 30, 1998 and U.S. Provisional Application No. 60/111,721, filed Dec. 9, 1998; the contents of both are hereby incorporated by reference.

BACKGROUND OF THE INVENTION

The present invention relates to a method of assisting a user in a medical self treatment, said self treatment comprising a plurality of actions.

The present invention also relates to a system/an apparatus for assisting a user in a medical self treatment, said self treatment comprising a plurality of actions.

In the following a user/patient will be a patient having diabetes.

For a number of years it has been possible to purchase various devices for the treatment of diabetes, e.g. for injecting insulin, for measuring blood sugar (such a device is referred to as BGM in the following), for withdrawing blood samples, and other accessories, the purpose of which is to enable the patient to nurse his disease discretely and with a high standard of safety.

Many diabetic patients are elderly people who can easily get insecure with respect to the medical equipment. It is very reassuring and therefore also very important that the user can have feedback from the system which confirms to the user that everything is OK right from the technical function of the system to the patient's physiological condition. This stretches out a psychological safety net under the patient, which contributes to improving the quality of life of patients having a disease such as diabetes.

Traditionally, diabetic people live under strict rules of "do's and don'ts". There is a historical need in order to comply with a therapeutic regimen. The purpose of this being a well controlled blood glucose level (BGL) and thereby a much lesser risk of later complications. This is a highly undesirably situation from a 'quality-of-life' point of view. It often results in bad mood—which is known to lead to a poor BGL regulation. Thus an evil circle is created which is hard for the diabetic to break.

Additionally, in certain cultures/societies there is a reluctance against using syringes/needles to administer medication and people therefore choose alternative ways to try to comply with a regimen. However, this often has the unfortunate result that people choose alternatives that do not fully or at all correspond to the optimal regimen and thereby choose wrong alternatives with adverse effects.

Further, the metabolism is a very complex and dynamic system. It is very hard to get and maintain an overview for the diabetic as many factors play a role. It is very likely that the diabetic looses an overview or relies on too simple rules of operation or eventually neglect the illness.

Various systems trying to ease the hazels of diabetes have been proposed over time. These systems have basically an accounting role and simply keep track of whatever input the user specifies. In these systems input of food and exercise are usually a task that the user needs to initiate. Systems that rely on the user to take action can be hard to make function well due to the user's reluctance to deal with it.

Patent specification WO 95/32480 discloses a medical information reporting system which has a patient sensor device controlled via a patient operated interface device by a micro-controller which writes data to a memory and a report writer. The specification further discloses a warning algorithm with zone boundary values which is specified by the user and consent to by a physician. This system simply keep track of whatever input the user specifies.

Patent specification WO 94/24929 discloses a patient support and monitoring system, which has a database located at a remote location for collection of information in a remote database from sensors and a medicine administration system. This system also keep track of whatever input the user specifies and may initiate a medical reaction on the basis of received parameters.

SUMMARY OF THE INVENTION

The object of the invention is to provide a method which provides a user with a freedom of operation with respect to a self-treatment.

This is achieved by guiding the user with respect to a self treatment by presenting options/possibilities in such a way that compliance to a regimen may be obtained in numerous ways.

More particularly, the invention relates to a method of assisting a user in a medical self treatment, said self treatment comprising a plurality of actions, said method comprising the steps of collecting in a one or more databases data representing values of parameters relevant for said self treatment, where said method further comprises the step of processing said one or more databases to provide the patient with the alternate choices between tow or more actions and a corresponding dose for each two or more actions.

Hereby, the user's self-treatments change from restrictions to possibilities thereby enhancing the overall 'quality-of-life' for the user and better ensuring that the user's self-treatment complies better or fully with a specified regimen by choosing proposed choices which complies with the regimen. This avoids that the user chooses actions and alternatives which do not fully or at all correspond to the optimal regimen due to a lack of a clear overview of the complex factors involved in the self-treatment.

By providing the user with a number of options he maychoose the one(s) he likes best and still obtain the right and full treatment instead of choosing the easiest and most appealing course of action on his own, which may be wrong or insufficient and result in adverse effects.

Additionally, the possibility of choices fulfilling a prescribed regimen makes the patient feel more in control of the treatment and enhances the therapeutic value of the treatment and improves the patient's ability to adapt his treatment to his daily life.

Additionally, the user's feeling of being ill is reduced, since the user has options of choices instead of a dictation of actions.

An additional object of the invention is to estimate one or more future values for one of said parameters, in order to obtain information of the user's condition in the near future, hereby enhancing the possibilities of presenting better/more relevant choices.

One way of estimating one or more future values may be done on the basis on a dynamic model representing the human metabolism.

An additional object of the invention is to provide effective monitoring of electronic data/information which are used by a patient for self-treatment of a disease, so that a greater level of safety, both functionally and emotionally, and an effective feedback to the patient are obtained.

The invention also relates to computer system having means for executing a program, where the program when executed is to make the computer execute the method according to claims 1–19.

By computer system is meant a system comprising processing means and being programmable at one time or another in order to execute a set of instructions/commands like a system for the self-treatment of a patient e.g. comprising one or more of sensor, medication administering device, data collection, and displaying means or a general computer system as a PC, laptop, palmtop, or a system having at least one device comprising a micro controller adapted to execute a program (either in hard- and/or software), and so on.

The invention further relates to a computer readable medium having a program recorded thereon, where the program when executed is to make the computer execute the method according to claims 1–19.

The computer readable medium may e.g. be a CD-ROM, magnetic disk, ROM circuit, a network connection or generally any medium that may provide a computer system with information of how to execute instructions/commands.

The above mentioned system and method need as good as possible data collection in order to present relevant and useful choices/proposals to the user. In a preferred embodiment a system/method relating to individual apparatuses, which are provided with electronic communications equipment so that the apparatuses—when in a state of mutual communication—frequently exchange information between them, are provided. Hereby a greater functional safety can be achieved and the total data capacity of the system can be increased, so that the feedback possibilities, e.g. of the system checking that every apparatus is OK and set up properly and of the patient be given a number of possible and up to date choices to choose from in a given situation, are increased.

The individual devices may be arranged for various respective functions relevant to the treatment of e.g. diabetes, such as: a lancet device, a body fluid analyser, one or more drug administration apparatuses for administering a predetermined dose of medication to the patient. Further, there may be a number of other aids which the diabetic patient uses, e.g. test strips for the blood analyser, needles, napkins for wiping off blood, extra insulin cartridge, glucose tablets, waste containers, etc.

The apparatuses according to the example may communicate information such as: amount of medication, type of medication, the concentration of relevant substances in the body e.g. body fluid level/concentration, time stamp, amount of food (e.g. amount or units of carbohydrate), measurement of physical activity, notification (e.g. alert and warning) to the patient, body characteristics (e.g. weight, blood pressure etc.) and inventory logistics. This ensures that relevant information, for e.g. a drug administration system like a doser, i.e. number of units of insulin, insulin type and time and date for administering, can automatically be stored, displayed, received and transmitted to and from all the relevant apparatuses and more particularly in one or more database accessible by a system/method for processing in order to obtain the results described above and later. The doser could also receive information regarding a predetermined number of units of insulin to be administered and automatically set the amount of medication to be administered by electromechanical means. In this way elderly and handicapped people do not have to set the relevant amount of medication themselves but just activate the doser and a confirmation of the actual administered dose may be used as input.

Other types of drug administration systems like an inhaler adapted to administer a dose of medication in an air stream or a tablet dispenser may be included instead or in combination with the doser. The inhaler and/or tablet dispenser may also communicate with the other units for relevant information like the doser according to the invention.

It is especially useful to transmit the data from all apparatuses to the functional master module/apparatus containing the highest priority program for safe keeping, calibration and updating of data and possible transmission to e.g. an external unit like a PC or database for further data acquisition, storage and processing. In this way the patient, a physician or an expert care-team can obtain the behavior over time of the patient, and a check for compliance to a diet or treatment given to the patient by a physician or an expert care-team can be made. This enhances the possibility of choices according to the invention.

Additionally, it is also possible for the patient to manually input information about the treatment. This information may be historic information as well as information about a future scheme (behavioral pattern) e.g. planned physical exercise, administering of insulin, intake of food and other medications. This information may be collected and thus serve as an electronic diabetes diary or may be used to notify the patient through the receiving means as to whether the planned actions are dangerous or not. The patient can further receive recommended amounts of medication, exercise, food, etc. from a physician, from an expert-team or automatically. All this information may be used to estimate one or more future parameter values, e.g. BGL.

It is evident that since the apparatuses are to be carried by the patient, there is a potential lack of space for an advanced input device e.g. a keyboard. Therefore, information which cannot be input on a standardized form e.g. personal comments on the treatment may be typed into the apparatus by the patient using a simple input device once and can subsequently be chosen from a list, if needed again.

Preferably, all the apparatuses of the system exchange information so that every apparatus (or at least every apparatus within range) is updated with the combined information, but still one particular apparatus is the link to any outside systems, so that every bit of information is mirrored for better safety and backup. This demands a greater amount of total memory capacity for the system.

For a BGM according to an embodiment of the invention the relevant information could be the time and date for measurement, measured level/concentration of blood glucose which could be stored or transmitted to another apparatus.

For a doser according to an embodiment of the invention the relevant information could be the type of medication (e.g. long acting or short acting insulin), number of units of insulin to be administered and the time and date of the administering. This information could both be set manually by the patient or remotely by a physician, an expert care-team or automatically.

For an inhaler according to an embodiment of the invention the relevant information could be the type of medication, the number of units of medication to be administered and the time and date of the administering. This information could both be set manually by the patient or remotely by a physician, an expert care-team or automatically.

For a storage container according to an embodiment of the invention the relevant information could be used to keep track of the contents of the container so that every time an object (e.g. cartridge, needle, etc.) is used, the storage container will update the inventory list. This list could be transferred to a unit of highest priority immediately or later, which could in turn update the patient's total holdings of objects, so that the system could notify the patient when he should order a new stock of objects in order to keep all the different proposed actions available. The ordering could also be done automatically by the system if the inventory list is transferred to an external unit, which greatly improves the confidence, comfort and safety of the patient.

For a tablet dispenser according to an embodiment of the invention the relevant information could be the number of dispensed tablets, the number of remaining tablets, the time of dispension and the type of dispensed tablets. The dispenser could store and/or communicate this information to an available unit of highest priority or other units within communication range.

In the following a preferred embodiment according to the invention is described in detail. This particular embodiment is meant as one example only of the invention and should not as such limit the scope of protection as claimed in the appended claims.

The term "Margin Maker" is used in the following for a method/system according to the invention.

The invention will now be explained in detail with reference to the FIGS. 1–8, in which

DETAILED DESCRIPTION OF THE INVENTION

Figure 1:
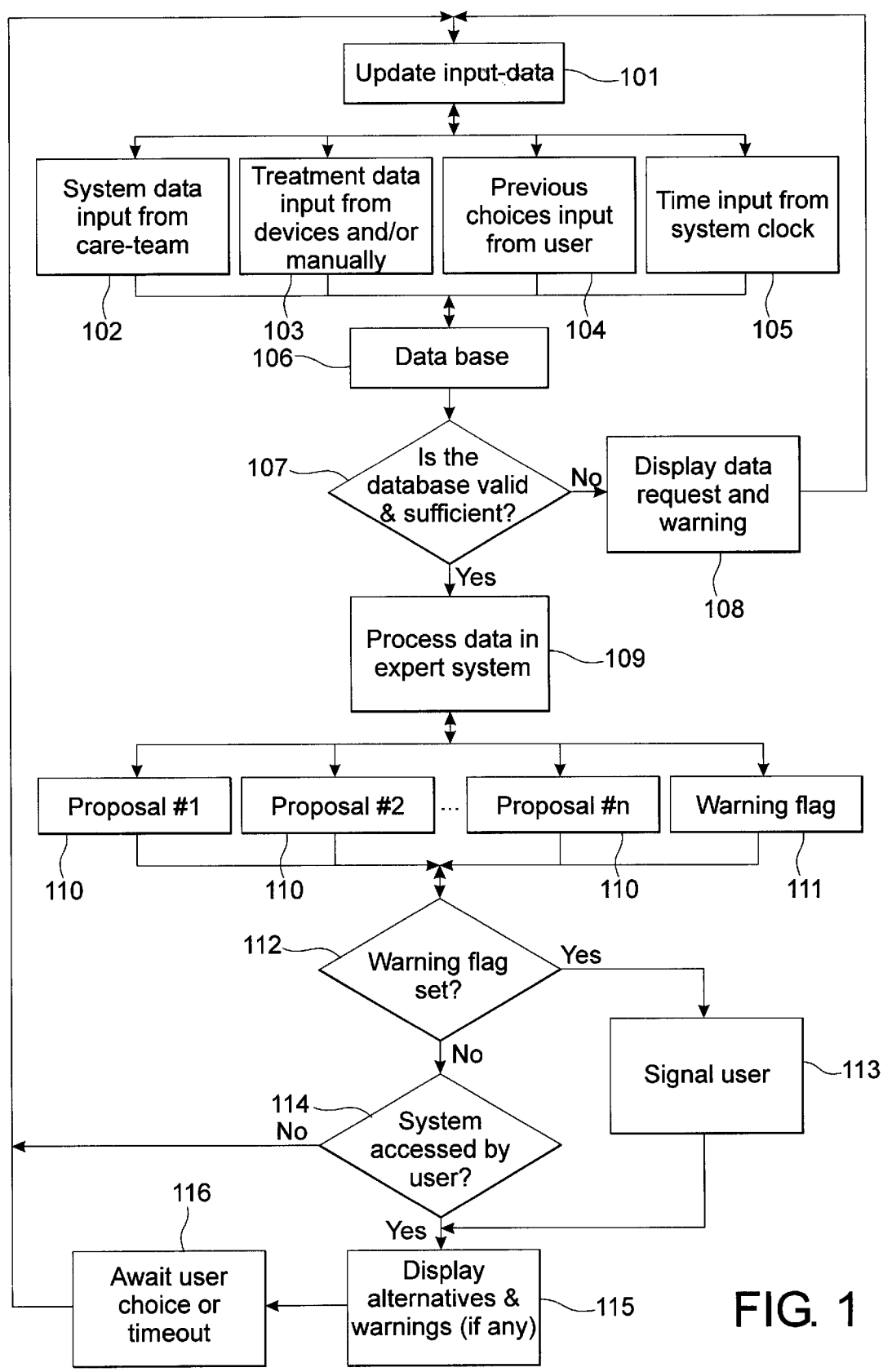
FIG. 1 shows a flowchart for an embodiment of the invention illustrating an exemplary implementation of a Margin Maker system.

FIG. 1 shows a flowchart for an embodiment of the invention illustrating an exemplary implementation of a Margin Maker system.

In step 101 input data is provided/updated. More specifically different types of input data are updated as represented by the steps 102–105.

In step 102 data from a care-team is provided/updated. This data describes individual user/patient characteristics which are true/valid in the time interval between consultations with the care-team. The data is typically derived as a result of tests performed by health care professionals (e.g. insulin sensitivity) and entered into the system by the care-team, e.g. wireless via a mobile telephone system as described in connection with FIG. 8.

In step 103 treatment input data is provided from various devices, e.g. from a system of portable apparatus as described above and in connection with FIGS. 5–7.

Input data specified manually by a user may also be input in step 103. Manually specified input data may e.g. be a value representing the body temperature of the user e.g. because he is feverish. Manually specified input may preferably if it differs from his normal value This data describes the actual treatment received by the patient (e.g. insulin intake as a function of time) and the resulting effect on the user (e.g. blood glucose level as a function of time). The data is gathered by the various devices used by the patient in his home-treatment and communicated automatically to the Margin Maker.

In step 104 the previous choices, i.e. input from the user, are provided/updated.

This is a record of the previous activities which the user has chosen to perform and which are either not yet confirmed by other input means (e.g. insulin injection prior to synchronization between the insulin doser an the Margin Maker) or not confirmable by other input means (e.g. physical exercise or food intake).

In step 105 information of time. is provided from a system clock in the form of a time stamp. Additionally the date may be specified as well.

It is necessary for the method to know the time because the alternative proposals available to the user change over time.

The information provided/updated in the steps 102–105 is collected in a database as a dataset at step 106.

Prior to processing the input data the system performs a test at step 107 to find out if the amount and/or quality of the input information is sufficient to produce valid and relevant proposals for user behaviour to present for the user of the Margin Maker system.

If the test fails, i.e. the input data is insufficient to produce a relevant output, the user is made aware of the fact that at the moment the Margin Maker is unable to offer guidance due to lack of input information and displays a request for more (comprehensive) data and issues a warning at step 108.

If the test is successful, the method continues in step 109, where the provided/inputted data is processed in an expert system e.g. using a model.

Figure 3:
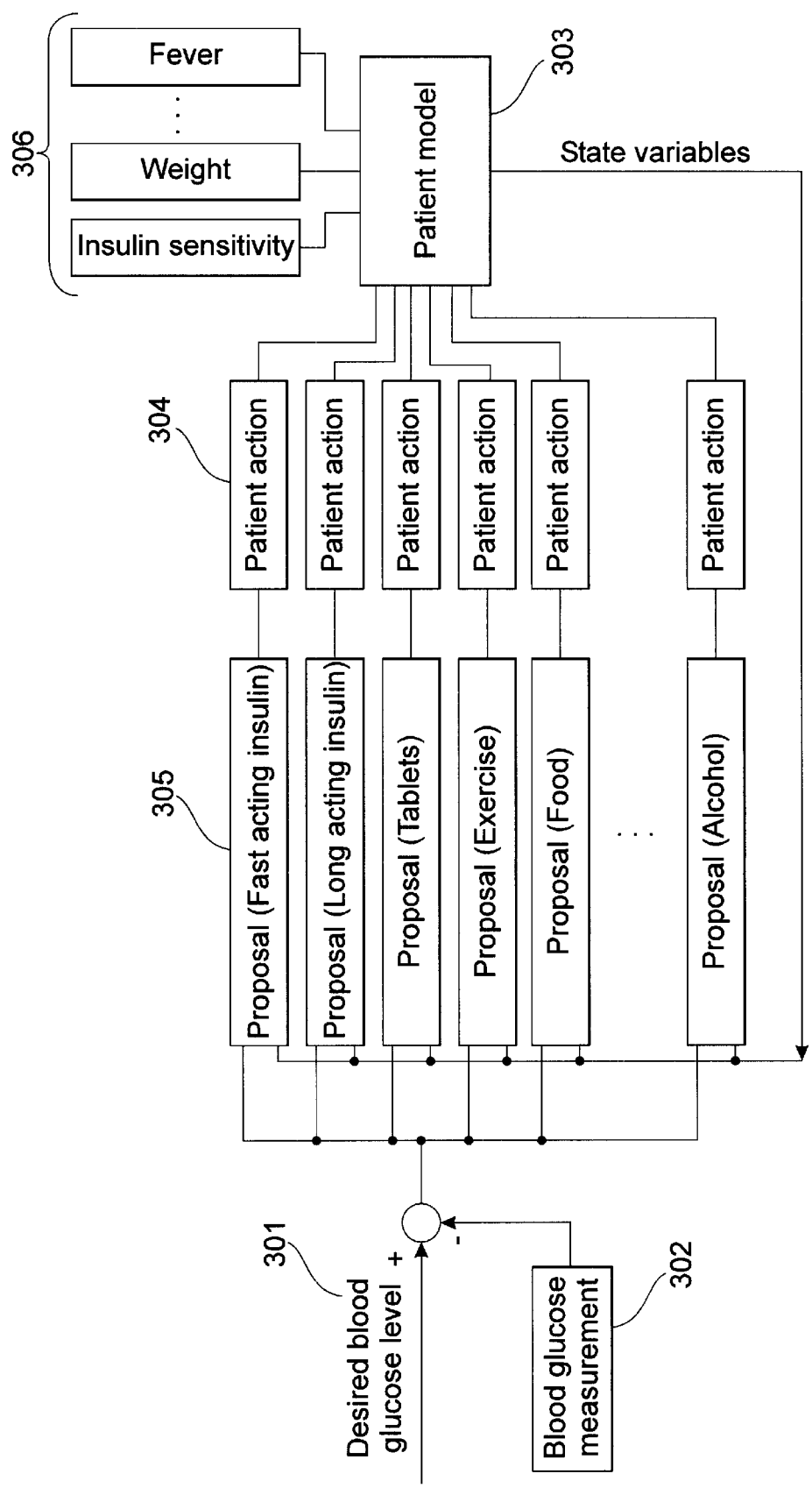
FIG. 3 illustrates a schematic diagram of an exemplary expert system using a model.
Figure 4:
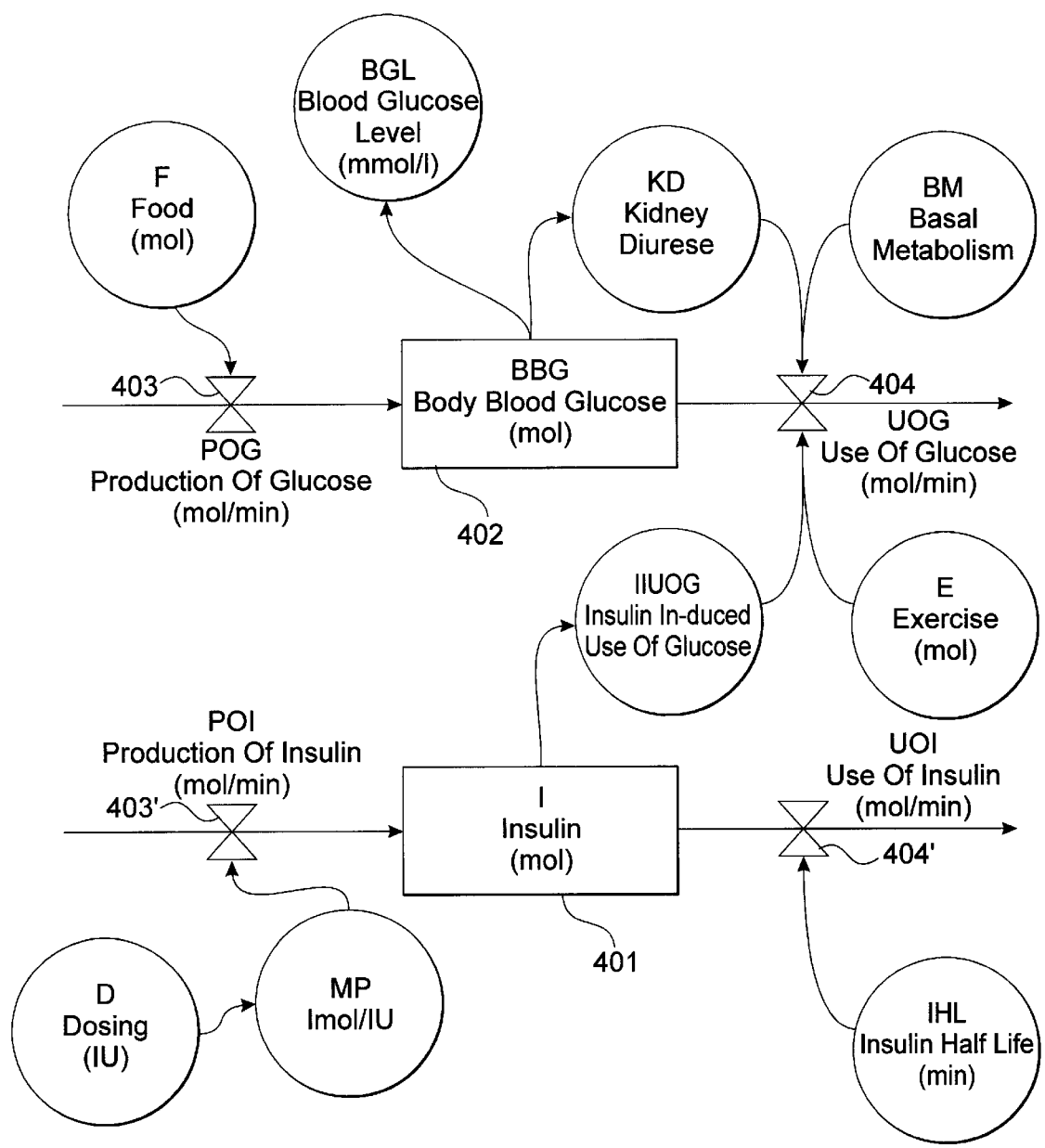
FIG. 4 shows a more detailed representation of a time dependent dynamic patient model according to the invention.

The expert system is in principle a model of a control loop for the blood glucose level in a human. Based on the input and the historical data accumulated in the Margin Maker the parameters of the model is adapted to mimic and predict the blood glucose control of the individual user of the Margin Maker system. Refer to FIGS. 3 and 4 for a more detailed description of the expert system.

For each of the n possible user actions implemented in the Margin Maker system the model is fed with information of the present blood glucose level, the target blood glucose level, the current time, the n−1 user actions set to their present value (ceteris paribus), and 1 user action is treated as a variable parameter. After n recalculations of the control loop, one for each of the n possible user actions treated as the variable parameter, the expert system has derived n ways of bringing the present blood glucose level to its target value. Then an evaluation of the n alternative proposals is needed in order to exclude proposals that are not implementable (e.g. it is not possible to eat a negative amount of food), thereby providing the 'up to n' valid and implementable proposals of possible choices 110.

In general, the sooner proposals are chosen, i.e. a situation is acted upon, the more options/proposals is available to the user. Put in another way, as the time goes the proposals/options become fewer and fewer as well as more and more restrictive, since the user's situation gets more and more serious, i.e. drifts away from a normal BGL, if not paid attention to/acted upon.

Another criteria for exclusion of proposals may e.g. be in a system, as described above, comprising different portable/handheld devices that the specific device being used to implement the proposal is present and activated among a user selected group of the devices. In this way the user will only be presented with proposals that he actually has the possibility of executing.

Finally, the time is considered variable in the expert system other things being equal to test whether a potentially dangerous situation is expected to occur within a given time frame. If this is found to be the case, a warning flag is set in step 111.

In step 112 a test whether the warning flag has been set is executed. If the test is true/yes (i.e. the warning flag has been set) a warning signal is sent to the user in step 113, regardless of whether the user is accessing the system, e.g. by audio to attract the user's attention and/or by activation of the display containing appropriate information. After the signal is given the method continues in step 115 where the warning and proposals are presented as will be described later.

If the test in step 112 results in false/no, another test is executed in step 114 as to whether the system is accessed by the user. If this is not the case, the method continues from the beginning in step 101 and awaits new and/or updated input since the present situation does not specifically require the attention of the user (warning flag not set).

If the test in step 114 is true and the user is accessing/has activated the system, step 115 is executed.

In step 115 the valid and implementable proposals are presented to the user. Any warnings are also displayed to the user if the preceding step was step 113 in order to alert the user and obtain an immediate action from the user. Issued warnings could e.g. comprise information that the user should seek medical attendance or administer a given medication as quickly as possible, etc.

Figure 2A:
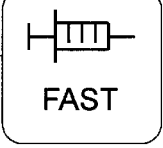
FIGS. 2a, 2b and 2c show examples of user interfaces presenting and receiving choices to and from a user.
Figure 2A:
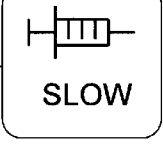
Figure 2A:
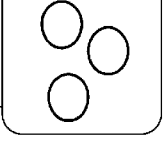
Figure 2A:
Figure 2A:
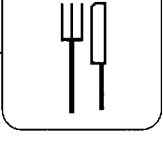
Figure 2A:
Figures 2B, 2C:
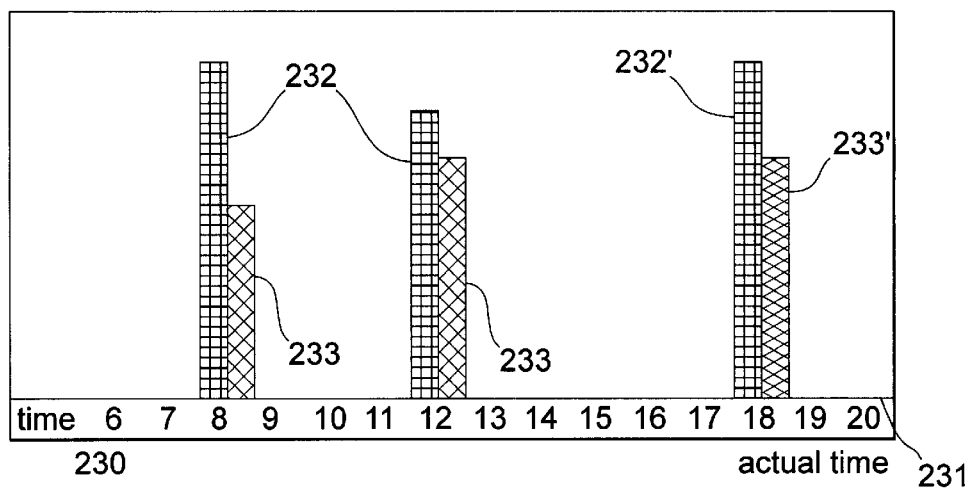

The proposals may e.g. be presented in the form shown in FIGS. 2a, 2b and 2c or other suitable forms.

In step 116 the system awaits a user choice of one of the proposed actions or a time out from the system.

Each of the proposals presented to the user of the Margin Maker will bring his/her blood glucose level "back on track" but that does not in any way exclude the possibility that the user chooses only to partly follow a suggested proposal, e.g. administering half the dose of medication instead of the proposed dosage, or to combine several proposals fully or in part. Once the user has entered his/her choice the Margin Maker performs a rerun of the flowchart to update the relevant proposals, given the new situation. An example of proposals and selected choices is shown in FIG. 2a.

If the user chooses to do nothing, the system will eventually issue a time out and perform a rerun of the flowchart to update the relevant proposals taking into account that time has elapsed since the last user action.

Hereby a user is presented with a number of choices each fulfilling a regimen where he may choose the one(s) he likes best and still obtain the right and full treatment instead of choosing the easiest and most appealing course of action on his own, which may be wrong or insufficient and result in adverse effects.

Additionally, the possibility of choices makes the patient feel more in control of the treatment and enhances the therapeutic value of the treatment and improves the patient's ability to adapt his treatment to his daily life.

FIGS. 2a, 2b and 2c show examples of user interfaces presenting and receiving choices to and from a user.

FIG. 2a shows an example of a user interface where one column 201 comprises different graphical icons 205–210 each representing one choice of action according to a proposal. Shown in this example are icons 205–210 for administering fast acting insulin 205, administering slow acting insulin 206, administering tablets of a given type 207, exercise 208, intake of food 209, and intake of alcohol 210. Additionally, other icons like administering tablets of another kind, administering a dosage medication from. an inhaler, etc. may be presented if these options are available to the user.

At column 202 the n proposals suggested by Margin Maker are shown (corresponds to step 115 in FIG. 1), where each proposal of action, if executed, brings the current BGL to the target BGL. In this example the Margin Maker has proposed to the user/patient either to administer 10 units (IU) of fast acting insulin, administer 0 IU of slow acting insulin, administer two tablets of a given type, exercise for 60 minutes, intake 0 units of food, or drink 0 units of alcohol.

At column 203 the user input is shown. After he has input the choice and amount of action, the Margin Maker displays and derives updated proposals on the basis of the changed situation. Here the user has chosen to administer 5 IU of fast acting insulin, and the Margin Maker now presents the updated proposals at column 202', given the new situation and taking into account the user's choice.

The updated proposals at column 202' are now to administer additionally 5 IU of fast acting insulin, administer 0 IU of slow acting insulin, administer one tablet of a given type, exercise for 30 minutes, intake 0 units of food, or drink 0 units of alcohol.

The user now chooses to exercise 30 minutes, which is shown at column 203', and the model updates the proposals accordingly. The proposals shown at column 202" show that after the user has performed the specified choices/actions his BGL should be at the target level.

The columns 204 represent previous and later proposals and user input, so it is possible to scroll through the values for different points in time.

This specific form of user interface requires a display of a certain quality or with a certain resolution. Other more simple forms may be provided, e.g. as shown in FIG. 2c, either instead or in combination in devices with a smaller display.

Alternatively, the display will only display one column of icons 201, proposals 202 and user input 203 at a time, e.g. with buttons to scroll through previous proposals and input.

The user may input data in many different ways according to specific embodiments of the invention as generally known in the art, e.g. utilising a touch screen with a stylus, touch pad and a cursor on the display, etc.

It is evident that if the apparatuses are to be carried by the patient, there is a potential lack of space for an advanced input device e.g. a keyboard. Therefore, information which cannot be input on a standardized form e.g. personal comments on the treatment is typed into the apparatus by the patient using a simple input device once and can subsequently be chosen from a list, if needed again.

Preferably, a system comprising a plurality of portable devices with mutual data communication, as described above, is used in connection with the Margin Maker.

In this way e.g. a doser may communicate an administered dose to the device containing the Margin Maker automatically or by user request and the different devices may communicate measured values representing physiological parameters automatically or by user request, e.g. a BGM may communicate the measured BGL as input to the Margin Maker.

Additionally, information of which devices are present and activated may be transmitted to the device containing the Margin Maker which may hereby only present proposals with a corresponding present and/or activated device, so that e.g. if a doser containing slow acting insulin is not available to the user, then the icon 206 and the corresponding proposal will not be displayed at all.

In FIG. 2b an example of a user interface is shown where input of information is given to the Margin Maker which is needed in order to derive the proposals of actions. Shown is a column 220 containing icons 224 representing a value obtained from the BGM and 225 representing a value for the temperature of the user. The corresponding values, specified at a given time, are listed in a column 221 and are in this example 10.5 mmol/l and 37.5° for the BGM and the temperature, respectively. The other columns 222 represents values specified at different points in time where in this example no values are specified. Alternatively, only columns having a specified value are shown in the user interface e.g. with a corresponding time stamp.

The columns 223 represent previous and later user input, so it is possible to scroll through the values for different points in time.

This information is used by the Margin Maker together with additional information to better estimate the target glucose level and obtain a measure of the present glucose level. The input temperature is used by the expert system to determine whether the user is feverish or not as this influences the required amount of insulin.

This information may either be input manually by the user, automatically or both, e.g. by a BGM device and/or a temperature sensor with communication means which may communicate with a Margin Maker device (may correspond to step 103 in FIG. 1).

FIG. 2c shows an example of a different user interface which may be more suited for a smaller display. Shown is an example of a graph 230 with a time axis 231 and three BGL bars 232 and 232 obtained at three different points in time of the day. Two previously obtained BGLs 232 and one BGL 232 obtained at the actual time. The BGL may be obtained from a BGM and may be received either automatically or manually by the Margin Maker as input for the expert system as described above.

Also shown are two bars 233 representing the dose of insulin, that the user chose to administer previously after obtaining the BGLs 232, respectively. The dosages 233 may have been fully or partly as proposed by the Margin Maker at the respective time. Alternatively, the user may have administered the dosages 233 completely on his own and just specified the dosage and type of medication. The actual dosages 233 administered may have been specified (together with the time and type of insulin) by user input or via communication from the administering doser to a device containing the Margin Maker.

The previously obtained BGLs 232 and administered dosages 233 together with the BGL 232, obtained at the actual time and other relevant input, as described in connection with FIG. 1, and used to predict a future course of BGL for the user and derive one or more proposals to the user in order to account for the future course of BGL.

The Margin Maker has proposed in this example that the user should administer a dosage as indicated by the blinking bar 233. Additionally, other proposals may be shown elsewhere. The proposed dosage and type of insulin may be transmitted automatically to a corresponding doser, so if the user wishes to follow this proposal fully he just has to activate a button on the doser to accurately receive the proposed dosage. Alternatively, the user may manually specify the proposed dosage on the doser.

Additionally, the user may choose to only administer a part of the proposed dosage (which may also be transmitted automatically after indication by the user) if he e.g. wants to exercise as well. After the Margin Maker has registered the users choice of only administering a part of the proposed dosage of medication, the expert system is updated accordingly and new proposals are derived taking into account the new situation.

The user interfaces described in connection with FIGS. 2a, 2b and 2c are just examples and other interfaces may be just as applicable. Alternatively, the user interface may be character based and using no graphics thereby reducing the complexity of the system with respect to implementation.

FIG. 3 illustrates a schematic diagram of an exemplary expert system using a model.

A number of models have been proposed in order to describe the metabolism of the insulin dependent diabetic patient. Furthermore, some effort has been put into constructing systems for controlling the blood glucose level using insulin.

In the following one expert system is described as an example but other expert systems known in the prior art may be used with similar results. The shown expert system comprises input variables 301 and 302, physiological parameters and model inputs 306, proposal generators 305, patient actions 304, and a patient model 303, all of which will be described in the following.

An input variable Desired blood glucose level 301 is specified in the expert system and is preferably (pre) determined by the care-team or other professionals. The variable 301 may be similar to the blood glucose level of a healthy person, but may due to regimen differ from this value, e.g. be higher in order to prevent hypoglycaemia.

Another input variable used by the expert system is the variable "Blood glucose measurement" 302 representing the BGL at a given time.

The patient may measure the BGL, giving the blood glucose measurement variable 302, with a certain frequency or use a continuous blood glucose sensor. Given the dynamics of the human metabolism, there is a certain lower limit of the sample frequency which will allow the expert system to work properly.

The patient model 303 is a dynamic model which describes the metabolism of the diabetic patient. The model 303 incorporates parameters 306 such as e.g. weight of the patient and insulin sensitivity, which vary from patient to patient and may be considered constant between consultations of the care-team. The model 303 may also incorporate model input 306 such as injections of long acting insulin, fast acting insulin, oral diabetic agents, exercise, food intake, alcohol intake and fever. Given a certain combination of model input 306, the model 303 describes the blood glucose level over time. The model 303 describes some key state variables of the human metabolism.

The proposal generators 305 are the analogy of regulators in a control system. The input to the proposal generators 305 is the difference between the desired blood glucose level 301 and the actual blood glucose level 302 and the state variables of the patient model. Given the input each proposal generator 305 proposes a patient action and a corresponding amount/dosage eat a certain amount of food, exercise for a certain amount of time, inject a certain amount of fast acting insulin, etc.—as indicated in the proposal boxes 305. The proposals are calculated, presuming that only one of the proposals is followed.

The patient has the final decision as indicated by patient action 304 for each possible action in the expert system. He may or may not choose to follow the proposals. By choosing one of the proposals fully or partly, his action 304 is fed into the patient model, either by manual input or automatically by the diabetes specific devices the dosers or the blood glucose monitor. The patient model 303 now generates a new input to the proposal generators 305 which represents the updated situation.

FIG. 4 shows a more detailed representation of a time dependent dynamic patient model according to the invention. This model is used by the expert system to give a prediction/estimate of a future BGL.

In the literature many such models are described. Here a very simple one of applicant's origin is taken to explain the principles. This model can be developed to a high degree of detail, if needed.

The model 400 simulates the dynamics of the carbohydrate metabolism. Based on the input of one or more of the following parameters

BGL, dosage of medication, type of medication, food intake, drinks intake, exercise, time stamp, insulin sensitivity weight of the user, blood pressure, temperature, and other.

The model is tuned in to mimic the user's carbohydrate metabolism closely. By the continuous tuning by input of updated data from the expert system a drift away from a close mimic of the true status is prevented. The structure of the model 400 matches the functionalities of the metabolism to a needed degree. Due to this correspondence the expert system/model 400 will be able to predict trends or even future BGL.

The expert system continuously gives suggestions about the user's freedom of operation. Based on all recorded events a margin for exercise and food is suggested.

If suggestions are confirmed (e.g. tapping an indication on the touch screen of the handheld device), these are regarded as input to the algorithm and used for future suggestions.

Preferably, the dialogue is implemented via a graphic display showing the history, and input is given either via a touch screen or traditional buttons.

In order for the expert system to give recommendations and margins as described above it is needed to predict how things will evolve from any known state.

This can be done using a model 400 of the carbohydrate metabolism as an engine for the Margin Maker concept.

Shown in the figure is a model 400 with two pools: Body Blood Glucose 402 and Insulin 401. Each has a filling source 403, 403 and a drain 404, 404 (i.e. two rates), respectively. Body Blood Glucose 402 has the filling source POG (Production of Glucose) 403 and the drain UOG (Use of Glucose) 404, and Insulin 401 has the filling source POI (Production of Insulin) 403 and the drain UOI (Use of Insulin) where all the rates 403, 403, 404 and 404 may vary with time dependent on the parameters controlling the rates.

The parameters controlling the rates, e.g. food, dosing, exercise, etc., are given in the table below.

The model 400 can also be expressed in terms of a set of differential equations for the states 402 and 401, each being controlled by their respective rates 403, 404 for the state Body Blood Glucose 402 and 403 and 404 for the state Insulin 401. In this form the model can be implemented in a microprocessor relatively easily and display the results of the latest input for any given time.

The differential equations for the model 400 may be expressed as:

$$BBG(t) = BBG(t-dt) + (POG - UOG) * dt$$

INFLOWS: POG=f(F,t)

OUTFLOWS: UOG=g(BM+KD+IIUOG+E,t)

$$I(t) = I(t-dt) + (POI - UOI) * dt$$

INFLOWS: POI=h(MPI,t)

OUTFLOWS: UOI=j(HL,t)

The factors are explained in the table below:

| Factor | Explanation | Unit | Function |
|---|---|---|---|
| Input/Output | | | |
| D | Dosing | IU | Output to the user about possible insulin doses to take. Alternatively the user can give input about a wanted amount of insulin and the system can suggest appropriate food intake. Whenever an insulin dose is taken the system automatically loads the value into the model and the predictions are calculated accordingly. |
| E | Exercise | mol | Output to the user about possible exercise to take in the given situation. Alternatively the user can give input about a wanted amount exercise and the system can suggest appropriate food intake. The user accepting the suggestion will be an input to the system and calculation will be accordingly. Conversion to mol will be made by the system. |
| F | Food intake | mol | Output to the user about possible food to take in the given situation. The user accepting the suggestion will work as an input to the system and calculation will be accordingly. Alternatively the user can give input about a wanted amount of food and the system can suggest either dosing of insulin or exercise. |

-continued

| Factor | Explanation | Unit | Function |
|---|---|---|---|
| | | | Conversion to mol will be made by the system. |
| Concentrations and levels | | | |
| BBG | Body Blood Glucose | mol | Simulated total amount of glucose in the blood. It is calculated as the integration over time of production and usage of glucose. Between measurements it is used to give an estimate of the user's current BGL. At measurements the BBG is updated according to the measured BGL. |
| BGL | Blood Glucose Level | mol/l | This calculated by dividing the BBG with the blood volume. The model has the ability to predict the BGL over time and the value is very important to the user and can be displayed at any time. Every time the user makes a measurement of the actual BGL this is automatically loaded into the model by the system and it overrules the calculated one and resets the model. Initial value: 5 mmol/l |
| I | Insulin | mol | Insulin level in the body. The model has the ability to predict the Insulin level over time. It is calculated as the integration over time of production and usage of insulin. The initial value is set by the physician according to measurements and can be calibrated by the physician when the user meets for consultations. |
| Rates | | | |
| POG | Production Of Glucose | mol/ min | This rate is driven by the food intake entered and accepted by the user. It is also a function of time as different types of food have different dynamic impact on BGL. |
| POI | Production Of Insulin | mol/ min | This rate is driven by the injected insulin through conversion factor (MPI). It is also a function of time as different types of insulin have different dynamic impacts on BGL. |
| UOI | Use Of Insulin | mol/ min | This rate is defined by the half life (IHL) of insulin by which the level decays exponentially. |
| UOG | Use Of Glucose | mol/ min | This rate is driven by 4 factors: Basal Metabolism (BM), Kidney Diurese (KD), Insulin Induced Use Of Glucose (IIUOG), Exercise (E). |
| Constants & Transfer functions | | | |
| BM | Basal Metabolism | mol/ min | Constant for each individual determined by the physician Typical value: 0.56 mol/min |
| IHL | Insulin Half Life | min | The metabolism of insulin is usually expressed in terms of half life. Typical value: 10 min |
| IIUOG | Insulin Induced Use Of Glucose | mol/ min | This factor describes the nonlinear relation between insulin in the body and the disappearance of glucose from the blood. This factor can be measured or derived from literature. |
| KD | Kidney Diurese | mol/ min | This factor describes the nonlinear relation between diurese and BGL. At BGL levels below 10 mmol/l the KD is virtually zero. Above 10 mmol/l an increasing KD will occur |
| MPI | Mol Per IU | mol/ IU | Conversion factor between International Units of insulin and mol |

This model 400 is just one relatively simple example of a model that may be used to predict a future BGL.

Alternatively, the model and/expert system or parts hereof may be located in a stationary unit with greater computational power and receive input and transmit information regarding proposed choices.

Figure 5:
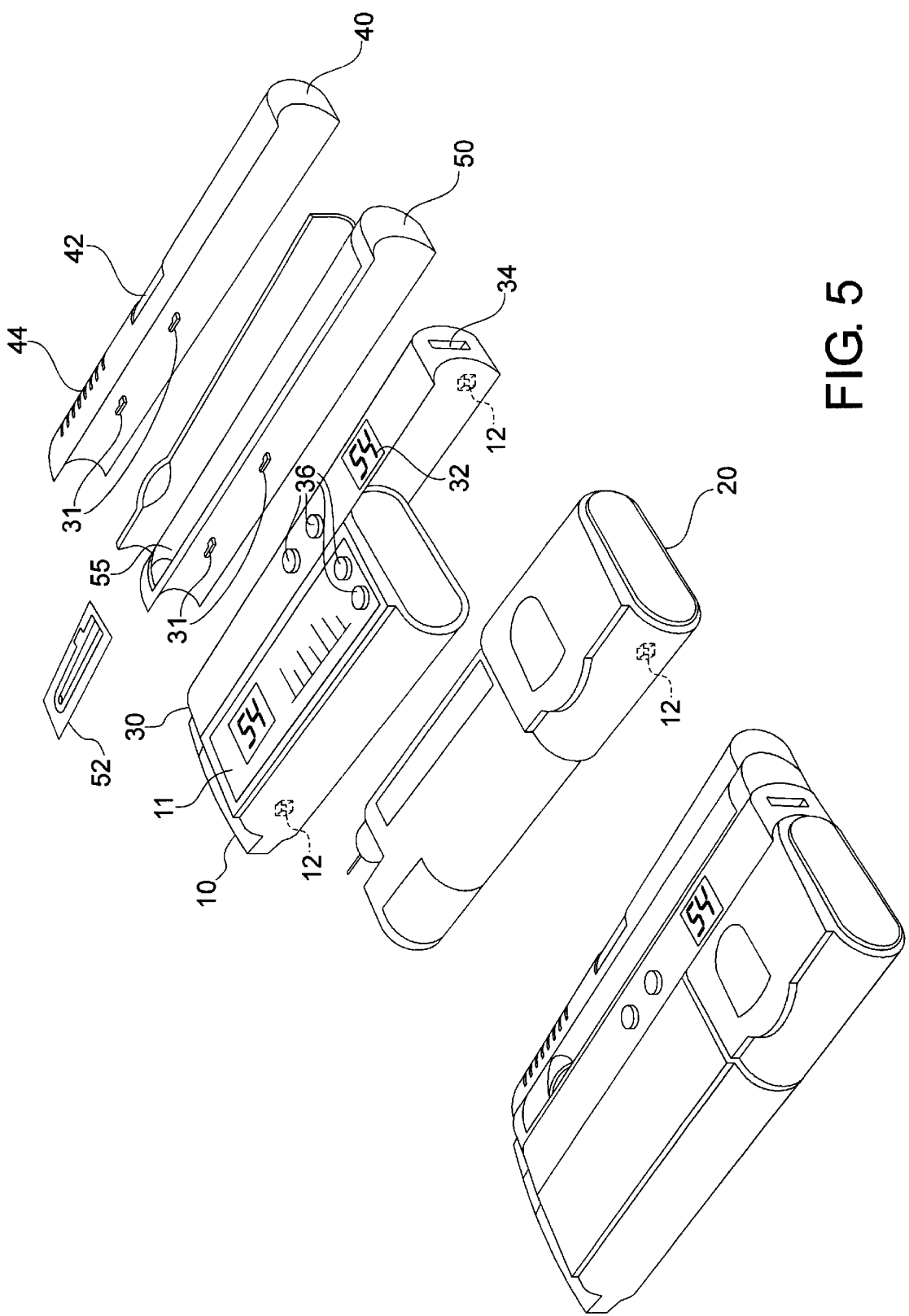
FIG. 5 shows an example of a preferred system which may contain an embodiment according to the invention.

FIG. 5 shows an example of a system which may contain an embodiment according to the invention.

Shown is a doser 20 with a cap 10 where the cap 10, in an embodiment, functions as the functional master module. In the preferred embodiment the Margin Maker resides in the functional master module. The functional master module 10 has displaying means 11 and buttons 36 for operation and selection of proposed choices.

The doser 20 is a conventional doser with has transmitting and receiving means 12. This enables the doser 20 to transmit stored data, i.e. the time, date, amount and type of medication, to the functional master module 10 for storage and presentation there via the master modules receiving means 12. Additionally, the transmitted data may be input to the Margin Maker automatically, thereby updating the model and deriving and presenting new proposals/choices, reflecting the updated situation, to the user on the display 11.

The doser 20 can also receive information via the receiving means 12 from the master module 10. This information could for instance be a predetermined amount of medication as dictated by a proposal from the Margin Maker if the user chooses to administer the full amount given by the proposal. The received information is then used to automatically set the correct amount of medication to be administered so that the patient does not have to worry about that aspect. Alternatively, if the user only wishes to administer only a part of the proposed dosage, he may indicate this via the buttons 36 or directly on the doser 20, after which information of the administered dose is sent to the Margin Maker as input and used to update the model.

Also shown is a BGM 30 which has means 34 for inserting test strips 52 containing a sample of blood, for analysis by the BGM 30 by operating the buttons 36. The result of the analysis is stored and either shown in the display 32 or transmitted to the master module 10 via the transmitting means 12 for storage and input to the Margin Maker and presentation on the larger display 11 or both. The patient can at the same time be presented with the last couple of results over a time period.

A test strip container 50 is provided for the safe keeping/ storing of test strips 52 in the space 55 and can be added/ attached through locking means 31. With this addition, a test strip 52 will always be available.

Further shown is a lancet device 40 removably attached to the BGM 30 or the test strip container 50 by the locking means 31. This lancet device 40 is used by first loading the lancet device through the grip 44 and then pressing the button 42, which releases the lancet, piercing the skin, so that a blood sample can be obtained. With this inclusion, the lancet device 40 is always at hand. This has the advantage that a lancet device 40 is always available, for taking a blood sample and applying it to a test strip 52. The test strip 52 can then be inserted via the means 34 into the BGM 30, which will start analysing the blood sample and, after completion of the analysis, will show the result in the display 32. It is very useful to have the BGM 30 and the lancet device 40 attached together in one compact unit, since a BGM 30 would not normally be used without the lancet device 40.

In this way, information relevant to the Margin Maker and the individual devices 20, 30 may automatically be received and transmitted between the functional master module 10 and the various devices 20, 30, which ensure an automatical update of the system.

Alternatively, the Margin Maker may only present choices to the user where there is a present and activated device for performing these choices (where applicable), e.g. a proposal of administering a certain amount of long acting insulin is only presented if a doser containing long acting insulin is present, or a doser and a separate cartridge containing long acting insulin. The functional master module is responsible for keeping track of which individual devices that are present and activated.

If the device containing the master module and/or the Margin Maker, the system may designate a new master module and a new Margin Maker either by transmitting and/or activating the relevant information in the designated device(s).

Figure 6:
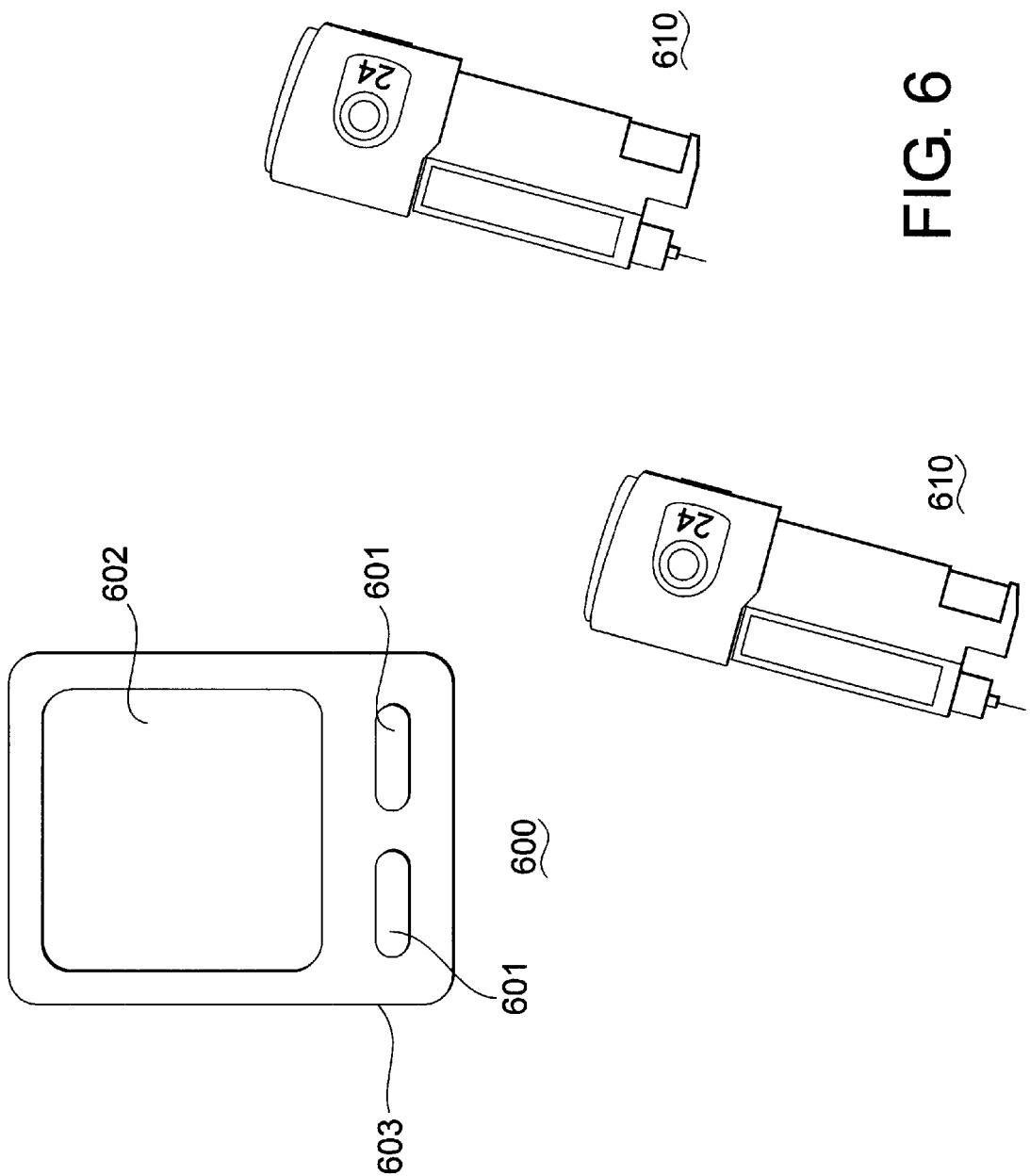
FIG. 6 shows another embodiment according to the invention.

FIG. 6 shows another embodiment according to the invention. Two dosers 610 are shown. The dosers 610 may contain different types of insulin (fast and slow acting). Also shown is a device 600 with a display 602, buttons for operation 601. In this particular embodiment the device 600 is both the functional master module and the Margin Maker. The device 600 is also provided with the functionality of a BGM and a slot 603 for receiving test strips containing a blood sample.

The dosers 610 and the BGM functionality may, together with user specified input e.g. a the device 600, provide the Margin Maker with relevant input information to the model and/or expert system, so that the Margin Maker may present the resulting choices on the display 602.

Figure 7:
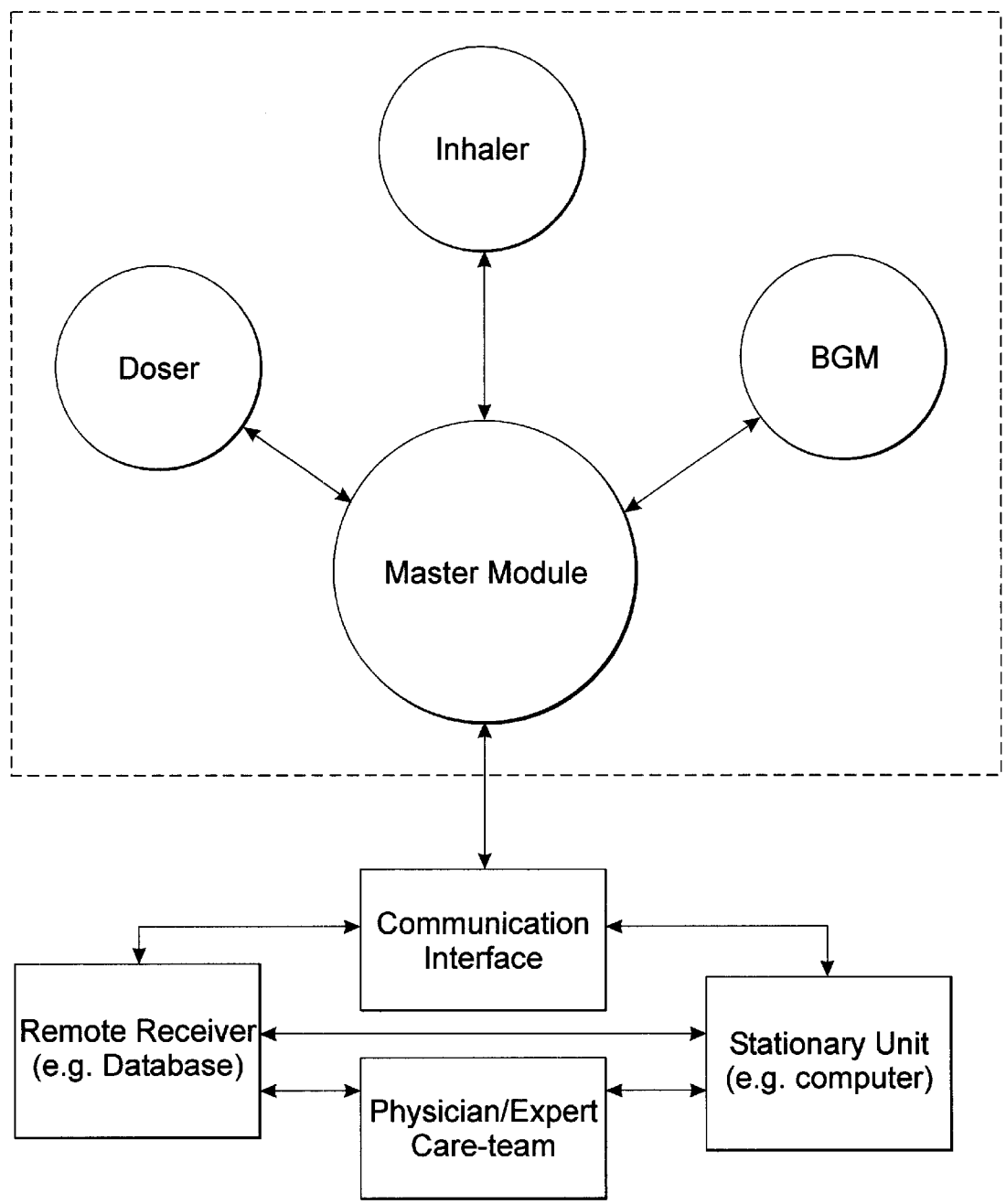
FIG. 7 illustrates the general concept according to an embodiment of the invention with respect to communication and exchange of information.

FIG. 7 illustrates the general concept according to an embodiment of the invention with respect to communication and exchange of information. Here the system consists of the portable units: a functional master module, a doser, a BGM, an inhaler, the remote units: Remote Receiver, Physician/Expert Care-team and Stationary Unit and a Communication Interface between them.

The functional master module controls the information and data flow between itself and the other apparatuses and collects relevant data and information from all the other portable units and uses this information to update the model accordingly. This data and information could e.g. be amount of medication, type of medication, body fluid concentration, time stamp (date and time) and inventory logistics. Additionally, the patient can manually input information and data related to amount of food, measurement of physical activity in the way described above.

This data and information can then be transmitted via a communication interface (which may be built into the master module) to external units like a database for data acquisition of the patient's data over time or a computer which the patient uses to be kept informed about his treatment. Alternatively, all the apparatuses could communicate to all the others.

The information in the database can be accessed by a physician or an expert care-team who could easily and quickly check for compliance to e.g. a diet or treatment course/progress. The physician or expert care-team could send a notification (e.g. alert, warning and/or change of regimen) to the patient if the data shows an inappropriate future treatment span. The patient could also be notified of a future appointment in this way or receive guidance.

The system gives the patient a number of choices to a given situation based on the model as described earlier. The patient could e.g. be informed that the blood glucose level/concentration is quite high and the patient could be presented with the choices of either exercising for given amount of time or administering a given amount of a given type of medication. The possibility of choices makes the patient feel more in control of the treatment and enhances the therapeutic value of the treatment.

Figure 8:
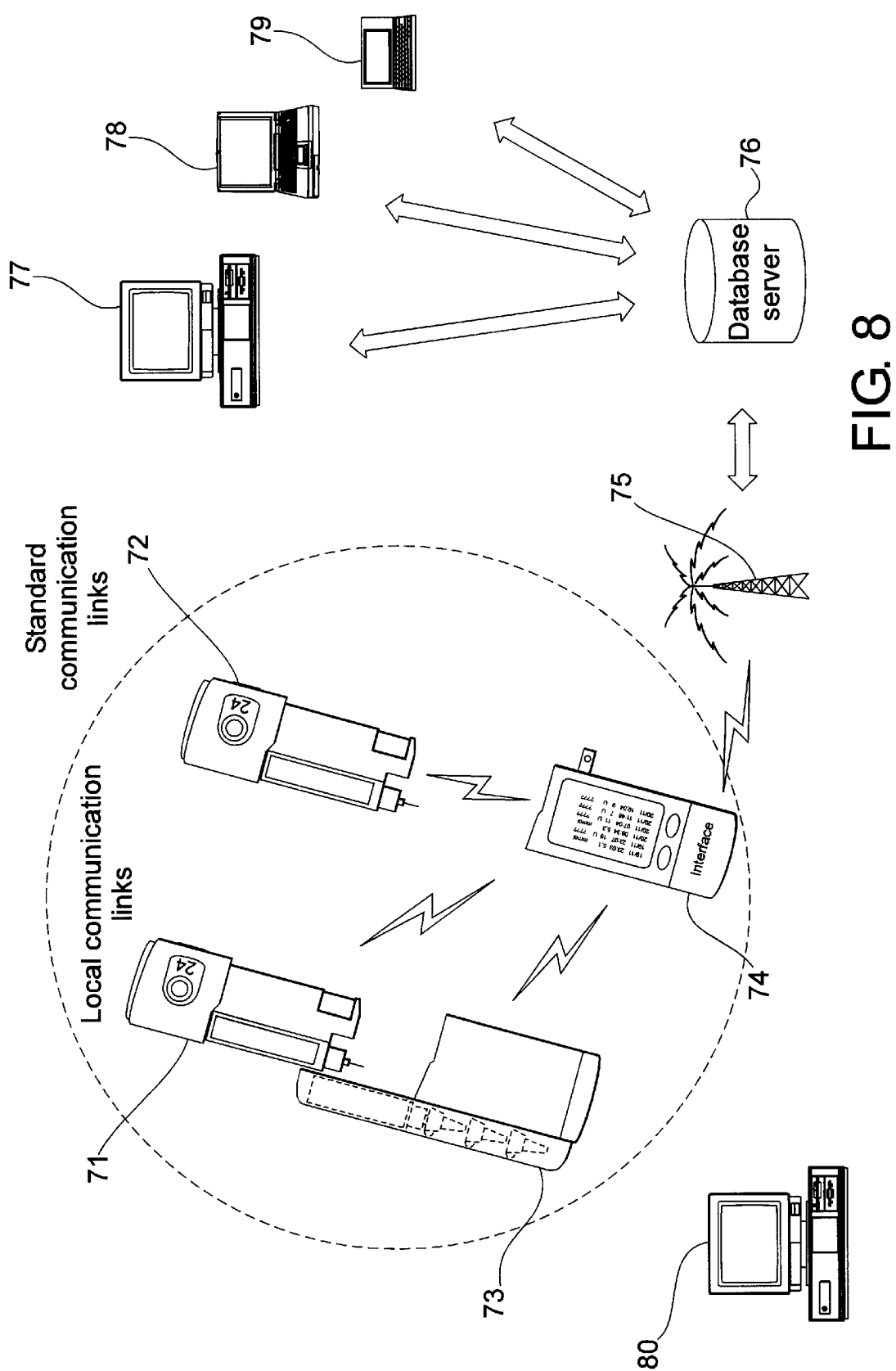
FIG. 8 illustrates the communication between a system of apparatuses and a central system.

FIG. 8 illustrates two dosers and their communication paths. The dosers are identical for the typical patient, one doser containing fast acting insulin, the other doser containing slow acting insulin. The dosers comprise a micro controller and memory. The dosers are capable of holding information about the insulin type they contain. This information may either be obtained by the doser reading e.g. a bar code on the cartridge or the information may be input from the patient. Thus the features of the doser enable it to log information about the insulin treatment (insulin type size of the dose and time stamp).

One doser is equipped with a cap unit 73 which acts as a storage container for an extra insulin cartridge, needles etc. The storage container is capable of keeping track of the contents of the container which enables it to keep the inventory list updated, as described earlier in the present document.

The other doser is equipped with a cap unit 74 comprising a BGM, a micro controller and memory. This enables the cap unit 74 to log information about the blood glucose concentration (with time stamp).

All the dosers 71,72 and the cap units 73, 74 comprise an interface which enables them to exchange data. In the present example the functional master device comprises the Margin Maker and is the BGM cap unit 74, which, in addition to the local interface, comprises an interface that enables it to communicate with external units through standard communication links (RS-232, Wireless local area network, phone, cellular phone, pager, satellite link, etc.). Through these communication links, the patient's treatment data can be transferred to the patient's own computer 80 or via e.g. the telephone system 75 to the patient's electronic medical record on a central server 76. From here, the treatment data may be accessed by the patient e.g. from a web page, using a stationary computer 77, a laptop computer 78, a handheld computer 79, etc. Apart from the patient, the care-team can access the patient's treatment data. The patient's master unit 74 can receive data from the central server 76, in addition to transmitting data.

This system has the advantage that the system can function on 3 levels: If one of the patient's devices 71, 72, 73, 74 is isolated by means of communication, it will log data.

When the patient's devices 71, 72, 73, 74 are within communication distance, the treatment data are transferred to the master unit 74, enabling it to supply the patient with an overview of his treatment and present choices as well as warnings or alarms if data shows that a potential dangerous situation may occur.

When the master device 74 is connected to the central server 76 through standard communication links, the treatment data is transferred to the patient's electronic medical record. This enables an expert system on the central server to notify the care-team if needed. The care-team may send information back to the user or send help if needed.

Furthermore it is well known that due to the safety of the patient, the development of a medical device is a time consuming task. Using a local communication form between the patient's devices 71, 72, 73, 74 has the advantage that only the master device 74 need to be redesigned to keep up with the continuous change in the standard communication links.

What is claimed is:

1. A method for assisting a patient in self-treating diabetes, the method comprising the steps of:

obtaining a value fin a blood glucose level from a patient with a blood glucose monitor; receiving other data relating to the patients condition;

collecting the value for the patient's blood glucose level and other data in one or more databases, wherein the collecting of blood glucose levels is accomplished automatically, without the user manually entering the blood glucose reading;

accessing the data with a processor;

analyzing the data with the processor wherein the analysis is automated sad performed using a data base engine means for proposing alternative treatment options; and based on the analysis, proposing two or more alternative choices for treating the patient based on the blood glucose level and other data inputted by the patient; wherein each choice presented will result in adequate blood glucose levels.

2. A method according to claim 1, characterized in that said method further comprises the step of estimating one or more future blood glucose level(s).

3. A method according to claim 1, characterized in that said step of estimating the future blood glucose level is done on the basis of a dynamic model representing a human metabolism.

4. A method according to claim 2, characterized in that said method further comprises the step of notifying said user if at least one of said one or more future values are outside a predetermined range of acceptable values.

5. A method according to claim 2, characterized in that said method further comprises the step of notifying a care-team/professional/central system if at least one of said one or more future values are outside a predetermined range of acceptable values.

6. A method according to claim 1, characterized in that said method further comprises the steps of registering one of said alternative choices selected by said user and registering a corresponding value specified by said user, and collecting in said one or more databases said registered choice and said registered corresponding value, wherein the registering steps may each be performed either automatically or manually or both.

7. A method according to claim 1, characterized in that said method further comprises the step of collecting in said one or more databases data representing the time.

8. A method according to claim 1, characterized in that said method further comprises the step of collecting in said one or more databases data specified by a care-team/professional/central system.

9. A method according to claim 2, characterized in that said one or more future values represents a predicted blood glucose level (BGL) at different future points in time.

10. A method according to claim 1, characterized in that said other data comprises one or more of blood glucose level (BGL), amount of administered medication, amount of administered insulin, type of medication, time stamp, amount of intake of food amount of intake of drinks, measurement of physical activity, insulin sensitivity, temperature blood pressure, and weight of said user 11. A method according to claim 1, characterized in that said other data comprises one or more of body fluid connection, amount of administered medication, type of medication, time stamp, amount of intake of food, amount of intake of drinks, measurement of physical activity.

insulin sensitivity, temperature blood pressure, weight of said user, insulin,

OHA (Oral Hyperglyehernical Agent),

HRT (Hormone Replacement Therapy), and growths hormones.

12. A method according to claim 1, characterized in that said alternative choices are selected from the group of administer slow acting insulin, administer fast acting insulin, administer tablets, exercise, intake food, and intake drinks.

13. A method according to claim 1, characterized in that said method further comprises the step of controlling data information between a plurality of portable apparatuses for use by a patient for medical self treatment, the treatment including a first action and at least a second action, said portable apparatuses comprising a first apparatus for performing the action operation, and at least a second apparatus for performing the second action, wherein:

each apparatus has a means for one or mere of the following: storing, transmitting, receiving, processing and displaying information, an attempted data communication between said apparatuses is initiated on request, said communication being controlled by a functional master module, designating said functional master module among at least two of said apparatuses, and designating a processing apparatus comprising said one or more databases among at least two of said apparatuses.

14. A method according to claim 13, characterized in that program information having the highest priority with respect to control and monitoring of mutual data communication between said apparatuses is stored/activated in said functional master module.

15. A method according to claim 13, characterized in that said method further comprises designating a new functional master module if the current designating master module becomes unavailable.

16. A method according to claim 13, characterized in that said method further comprises designating a new processing apparatus if the current designated processing apparatus becomes unavailable.

17. A method characterized in that said method further comprises the step of representing values of parameters relevant for said self treatment from one or more of said portable apparatuses.

18. A method according to claim 13, characterized in that said method further comprises the step of selecting one or more portable apparatuses which is present and active from all the portable apparatuses and presenting corresponding choices only for the selected one or more portable apparatuses.

19. A computer system having means for executing a program, where the program when executed is to make the computer execute the method according to claim 1.

20. A computer readable medium having a program recorded thereon, where the program when executed is to make the computer execute the method according to claim 1.

21. The method of claim 1, wherein the other data is automatically collected without the need for the patient to manually enter the data.

22. The method of claim 1, wherein the other data is manually inputted.

23. The method of claim 1, wherein some of the other data is automatically collected and some of the other data is inputted by the patient.

24. A system for assisting in the self-treatment of diabetes, the system comprising:
    one or more databases for storing data relating to the patients condition;
    a means for automatically collecting blood glucose data and sending it to at least one of the databases; and
    a processor for accessing the data, the processor configured to analyze the data with a database engine means for proposing two or more alternative choices for treating the patient based oil the blood glucose level and other data inputted by the patient wherein each choice presented will result in adequate blood glucose levels.

25. An apparatus for assisting a patient in self-treating diabetes, comprising:
    a means for obtaining a value for a blood glucose level from a patient with a blood glucose monitor;
    a means for receiving other data relating to the patients condition;
    a means for collecting the value for the patient's blood glucose level and other data in one or more databases, wherein the downloading of blood glucose levels is accomplished automatically, without the user manually entering the blood glucose reading;
    a means for accessing the data with a processor;
    a means for analyzing the data with the processor, the processor configured to analyze the data with a database engine means for proposing two or more alternative choices for treating the patient based on the blood glucose level and other data inputted by the patient; and wherein each choice presented will result in adequate blood glucose levels.

26. An apparatus according to claim 25, further comprising a means for estimating one or more future blood glucose levels.

27. An apparatus according to claim 26, wherein the a means for estimating one or more future valves utilizes a dynamic model representing a human metabolism.

28. An apparatus according to claim 26, further comprising a means for notifying said user if at least one of said one or more future values are outside a predetermined range of acceptable values.

29. An apparatus according to claim 26, further comprising a means for notifying a care-team/professional/central system if at least one of said one or more future values are outside a predetermined range of acceptable values.

30. An apparatus to claim 25, further comprising means for;
    registering one of said alternative choices selected by said user and registering a corresponding value specified by said user, and
    collecting in said one or more databases said registered choice and said registered corresponding value.

31. An apparatus according to claim 25, further comprising a means for collecting in said one or more databases data representing the tine.

32. An apparatus according to claim 25, further comprising a means for collecting in said one or more databases data specified by a care-team/professional/central system.

33. An apparatus according to claim 26, wherein one or more future values represents a predicted blood glucose level (BGL) at different future points in time.

34. An apparatus according to claim 25, wherein said other data comprises one or more of
    a. blood glucose level (BGL)
    b. amount of administered medication,
    c. amount of administered insulin,
    d. type of medication,
    e. time stamp,
    f. amount of intake of food
    g. amount of intake of drinks,
    h. measurement of physical activity,
    i. insulin sensitivity,
    j. temperature,
    k. blood pressure, and
    l. weight of said user 35. An apparatus according to claim 25, wherein said other data comprises one or more of
    body fluid concentration,
    amount of administered medication,
    type of medication,
    time stamp,
    amount of intake of food,
    amount of intake of drinks,
    measurement of physical activity,
    insulin sensitivity,
    temperature,
    blood pressure, and
    weight of said use.
    insulin,
    OHA(Oral Hyperglychemical Agent)
    HRT(Hormone Replacement Therapy), and
    growths hormones.

36. An apparatus according to claim 25, characterized in that said alternative choices are selected from the group of
    administer slow acting insulin,
    administer fast acting insulin,
    administer tablets,
    exercise,
    intake food, and
    intake drinks.

37. An apparatus according to claim 25, further comprising a means for controlling data information between a plurality of portable apparatuses for use by a patient for medical self treatment, the treatment including a first action and at least a second action, said portable apparatuses comprising a first apparatus for performing the action operation, and at least a second apparatus for performing the second action wherein:

each apparatus has a means for one or more of the following: storing, transmitting, receiving processing and displaying information, an attempted data communication between said apparatuses is initiated on request, said communication being controlled by a functional master module, designating said functional master module among at least two of said apparatuses, and designating a processing apparatus comprising said one or more databases among at least two of said apparatuses.

38. An apparatus according to claim 37, characterized in that program information having the highest priority with respect to control and monitoring of mutual data communication between said apparatuses is stored/activated in said functional master module.

39. An apparatus according to claim 37, further comprising a means for designating a new functional master module if the current designating master module becomes unavailable.

40. An apparatus according to claim 37, further comprising a means for designating a new processing apparatus if the current designated processing apparatus becomes unavailable 41. An apparatus according to claim 40, further comprising a means for receiving said data representing values of parameters relevant for said self treatment from one or more of said portable apparatuses.

42. An apparatus according to claim 40, further comprising a means for selecting one or more portable apparatuses which is present and active from all the portable apparatuses and presenting corresponding choices only for the selected one or more portable apparatuses.

43. The apparatus of claim 25, further comprising a means for automatically collecting the data without the need for the patient to manually enter the data.

44. The apparatus of claim 25, comprising a means for manually entering the other data.

45. The apparatus of claim 25, further comprising a manual entry means and an automatic entry means whereby some of the other data is automatically collected and some of the other data is inputted by a patient.

46. An apparatus for assisting a patient in self-treating diabetes, comprising:

a means for obtaining a value for a blood glucose level from a patient, a means for receiving and storing a patient's blood glucose and other data relating to the patients condition;

a means for accessing and analyzing the blood glucose level and the other data with a processor, wherein the processor is configured to analyze the data wit a database engine means for proposing two or more alternative choices for treating the patient based on the blood glucose level and other data inputted by the patient; and wherein each choice presented will result in adequate blood glucose levels.

* * * * *